United States Patent [19]

Lotze et al.

[11] Patent Number: 5,252,764
[45] Date of Patent: Oct. 12, 1993

[54] PREPARATION OF GOLD (I) MERCAPTIDES

[75] Inventors: Marion Lotze, Hammersbach; Margit Bauer, Bunderspulik, both of Fed. Rep. of Germany

[73] Assignee: Degussa Aktiengesellschaft, Frankfurt am Main, Fed. Rep. of Germany

[21] Appl. No.: 984,723

[22] Filed: Dec. 4, 1992

Related U.S. Application Data

[63] Continuation of Ser. No. 807,231, Dec. 16, 1991, abandoned.

[30] Foreign Application Priority Data

Dec. 18, 1990 [DE] Fed. Rep. of Germany ....... 4040447

[51] Int. Cl.$^5$ .................. C07C 321/04; C07C 321/00
[52] U.S. Cl. .................................................. 556/113
[58] Field of Search ........................................ 556/113

[56] References Cited

U.S. PATENT DOCUMENTS

| | | |
|---|---|---|
| 2,984,575 | 5/1961 | Fitch ................................. 556/113 |
| 3,022,177 | 2/1962 | Fitch . |
| 3,163,665 | 12/1964 | Fitch ................................. 556/113 |
| 3,245,809 | 4/1966 | Fitch . |
| 3,268,568 | 8/1966 | Fitch . |
| 3,345,199 | 10/1967 | Fitch . |
| 4,221,826 | 9/1980 | Baltrushaitis et al. . |

OTHER PUBLICATIONS

Chemical Abstract, vol. 84, No. 6, Feb. 9, 1976, Abstract No. 35807e.
Chemical Abstract, vol. 111, No. 4, Jul. 24, 1989, Abstract No. 32688g.
Hackh's Chemical Dictionary, McGraw Hill, NY, 1969, p. 27.

*Primary Examiner*—Marianne M. Cintins
*Assistant Examiner*—Rebecca Cook
*Attorney, Agent, or Firm*—Beveridge, DeGrandi, Weilacher & Young

[57] ABSTRACT

The known preparation of gold(I) mercaptides by means of reacting a gold(I) halogenide dialkyl sulfide complex, obtainable from a gold(III) halogenide or gold(III) halogen complex and a sulfide, with a mercaptan can be improved if a ($C_1$- to $C_8$-)-alkyl mercapto-($C_3$- to $C_6$-) amino acid or a water-soluble salt thereof is used as organic sulfide. The advantages of the sulfides of the invention over the previously used sulfides reside in their water solubility and insolubility in solvents and therewith in a simplification of the purification of gold(I) mercaptides independently of their structure and solubility. A further advantage of alkyl mercapto amino acids, especially D,L methionine, is their odor, which is much less than that of the ($C_1$-$C_8$) alkyl sulfides previously used.

22 Claims, No Drawings

PREPARATION OF GOLD (I) MERCAPTIDES

This application is a continuation of application Ser. No. 07/807,231, now abandoned, filed Dec. 16, 1991, which application is entirely incorporated herein by reference.

BACKGROUND TO THE INVENTION

The present invention relates to a method of preparing gold(I) mercaptides of the formula AU—S—R by reacting a gold(I) halogenide sulfide complex, obtainable from a gold(III) halogenide or gold(III) halogen complex and a sulfide, with a mercapto compound of the formula R—S—H.

Aliphatic, cycloaliphatic and aromatic gold(I) mercaptides of the general formula Au—S—R, in which R represents an organic group and in which the sulfur is bound to an aliphatic, cycloaliphatic or aromatic C-atom of the R group have long been known. The scope and definition of R, the organic group, are well recognized in the art. Such mercaptides are used in so-called gold preparations for the gilding of solid articles, especially ceramic materials, as components in luster preparations, and for producing strip conductors in integrated circuits.

A survey of the methods of preparing gold(I) mercaptides and of their use is contained in German patents 12 84 808, 12 86 866, 12 98 828; and U.S. Pat. Nos. 4,221,826 and 3,245,809 and 3,163,665 and 2,984,575 which U.S. patents are incorporated by reference, especially for the definition of R, the organic group.

According to these patents, two methods are known for preparing gold(I) mercaptides of the formula R—S—Au:

(A) $3 RSH + AuX_3 \rightarrow RSAU + R—S—S—R + 3 HX$
(B) $2 R'_2S + AUX_3 + H_2O \rightarrow AuX \cdot R'_2S + R'_2SO + 2 HX$
$AUX \cdot R'_2S + RSH \rightarrow RSAU + R'_2S + HX$.

Method A comprises the reaction of a gold(III) halogenide with three equivalents of mercaptan in the presence of an organic solvent. The gold(III) halogenide is reduced by means of two equivalents of mercaptan with the formation of disulfide to produce the gold(I) halogenide, which reacts immediately in the presence of the third equivalent of mercaptan to form the gold(I) mercaptide.

Method A is disqualified by the loss of two equivalents of mercaptan. As a rule, the mercaptans are chemically tailor-made compounds designed for their intended application and are thus too expensive to be utilized as a reducing agent. In addition, the separation of the gold(I) mercaptide from the disulfide is very expensive, requires large amounts of organic solvent, and frequently results in yield losses.

In the case of method B, the reduction of the gold(III) halogenide and its complex formation is carried out in the presence of at least one equivalent of water and two equivalents of a dialkyl sulfide. The gold(I) halogenide dialkyl sulfide complex compound formed thereby reacts with the mercaptan to form the gold(I) mercaptide with liberation of the dialkyl sulfide. One equivalent of dialkyl sulfide accumulates as a byproduct of the reduction stage.

In method B, a dialkyl sulfide such as dimethyl-, diethyl-, dibutyl- or dioctyl sulfide (which is more economical than the tailor-made mercaptan of method A) can be used as the reducing agent. In method B, the reaction mixture normally contains, after the reaction per equivalent gold(I) mercaptide, one to two equivalents of dialkyl sulfide and one equivalent of dialkyl sulfoxide which must be separated from the gold(I) mercaptide.

A disadvantage of method B is the fact that the previously used dialkyl sulfides are found to be undesirable from a work environment viewpoint on account of their penetrating odor. Even in the gold(I) mercaptides produced, traces of still-remaining dialkyl sulfide cause considerable odor problems.

Whereas the sulfoxides of the previously named dialkyl sulfides are sufficiently water-soluble and can generally be satisfactorily separated during the workup of the reaction mixtures from the gold(I) mercaptides, the alkyl sulfides themselves are non-water-soluble. The alkyl sulfides must therefore be separated by means of organic solvents from the gold(I) mercaptide. These solvents must be carefully selected as they should dissolve only the dialkyl sulfide but not the gold(I) mercaptide. The dialkyl sulfides can usually not be completely separated by washing out the usually solid gold(I) mercaptides, as the examples in the above-named patents show. A reprecipitation is required in most instances. However, such a reprecipitation is limited to gold(I) mercaptides soluble in organic solvents.

In an attempt to improve the previously known methods, Applicants also used water-soluble dialkyl sulfides (such as bis-hydroxyethyl sulfide and 2,2'-thiodiacetic acid) in the methods in question. It turned out as a result that the desired reactions did take place but the solubility of the named sulfides in organic solvents (such as dichloromethane, toluene, acetone, and ethanol) is so great that the above-mentioned problems occur in the preparation, isolation and purification of readily soluble gold(I) mercaptides in the presence of organic solvents.

SUMMARY OF THE INVENTION

An object of the present invention was to improve the method according to reaction principle B in such a manner that the gold(I) mercaptide formed can be separated independently of its structure and solubility in a simple manner, and can be separated completely from the sulfide and corresponding sulfoxide of said sulfide used.

Another object was to find a sulfide which exhibits as low an odor as possible and is capable of the required complex formation and formation of gold(I) mercaptide in as quantitative a yield as possible.

Finally, another object was to keep the technical expense and the amount of organic solvents for the workup of the reaction mixture and purification of the gold(I) mercaptide as low as possible.

According to the present invention, these and other problems are solved by means of a method for the preparation of gold(I) mercaptides of the formula Au—S—R, in which R is an organic group, by reacting a gold(III) halogenide, or gold(III) halogen complex, with a sulfide in a molar ratio of 1:2 to 1:3, preferably at the stoichiometric ratio of 1:2, in the presence of an amount of water at least equivalent to the AU(III) compound at $-20°$ to $40°$ C. The reaction mixture results in the formation of the gold(I) halogenide- sulfide complex and of said sulfide sulfoxide. The gold (I) halogenide sulfide complex is reacted at $-20°$ to $40°$ C. and, if necessary, in the presence of an organic solvent or solvent mixture with a mercaptan of the formula RSH, in which R has the same meaning as in the gold(I) mercaptides. Isolation of the resulting gold(I) mercaptide from the reaction mixture can be carried out in a known manner. Preferably an equimolar ratio of gold (I) sulfide complex: mercaptan is used, but an excess of mercaptan is possible (up to 1:2). A ($C_1$- to $C_8$-) alkyl mercapto-($C_3$- to $C_6$-) amino acid in which the alkyl mercapto- and the amino group are bound to different C atoms, or a water-soluble salt thereof, is used as the sulfide.

DETAILED DESCRIPTION OF THE INVENTION

The sulfides to be used in accordance with the present invention carry the alkyl mercapto group and amino group on different C atoms of the carboxylic acid. The carboxylic acid contains 3 to 6 C atoms and can be linear or branched. The amino group can be vicinal to the carboxyl group or separated by several C atoms; the same applies to the alkyl mercapto group as regards the carboxyl- and amino group. The alkyl group of the alkyl mercapto group can be linear or branched and contains 1 to 8 C atoms; preferably $C_1$- to $C_4$-alkyl, and especially methyl. The amino acid group of the preferred sulfides contains 3 to 4 C atoms. On account of their ready availability, alkylated cysteine and especially methionine are preferred sulfides. These alkyl mercapto amino acids are preferably used in the D,L form.

Salts of the sulfides to be used in accordance with the present invention include especially salts of alkyl mercapto amino acids with strong acids such as e.g. hydrohalic acid, sulfuric acid, phosphoric acid, perchloric acid. Salts such as the hydrochlorides are preferred. These result in stable gold(I) halogenide sulfide complexes. In principle, alkali- or ammonium salts of alkyl mercapto amino acid can also be used.

Gold(I) mercaptides of the general formula R—S—AU denote monomeric and aggregated forms of gold(I) mercaptides. The sulfur atom is bound to an aliphatic, cycloaliphatic or aromatic C atom of the organic R group, which can comprise one or several functional groups such as e.g. ester-, hydroxyl-, ether- or olefinic groups. Exemplary gold(I) mercaptides are described in the prior art cited above. Such gold (I) mercaptides include gold secondary mercaptides having the formula

wherein R and R' are alkyl, cycloalkyl, aryl or aralkyl radicals. Alkyl radicals which can be present as the R or R' of the foregoing formula for the gold secondary mercaptides include methyl, ethyl, butyl, isobutyl, heptyl, dodecyl, and octadecyl. Examples of the cycloalkyl radicals include cyclobutyl, cyclopentyl, and cyclohexyl. The aryl radicals include phenyl, naphthyl, and phenanthryl. Examples of the aralkyl radicals include benzyl, 2-phenylethyl, and 4-phenylbutyl.

Such gold I) mercaptides also include gold tertiary mercaptides having the formula

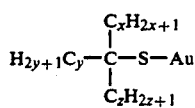

in which x, y and z are integers from 1 to about 40.

Such gold I) mercaptides further include gold aryl mercaptides having the formula Ar—S—Au wherein Ar is an aryl radical and the mercapto sulfur is attached directly to an aromatic ring of the aryl radical. Aryl radicals which can be present as the Ar of the foregoing formula include mononuclear and polynuclear radicals. Exemplary of such aryl radicals are phenyl, toly, xylyl, naphthyl, anthryl, phenanthryl, halogenophenyl, aminophenyl and carboxyphenyl, The aryl radicals also includes those aryl radicals in which at least one alkyl group containing at least three carbon atoms and preferably from about 4–12 carbon atoms is directly attached to an aromatic ring of the aryl nucleus.

$AuCl_3$, $AuBr_3$ and $AuI_3$ are used as gold(III) halogenide. Among the gold(III) halogen complexes, $HAuCl_4$ (tetrachloro auric acid) $HAuBr_4$ and $HAuI_4$ are preferred and tetrachloro auric acid is especially suitable. Complexes of the named AU(III) halogenides with a neutral ligand such as e.g. a tertiary amine or tertiary phosphine can also be used.

In general, the stage of the formation of the gold(I) halogenide sulfide complex and the reaction with the mercaptan of formula RSH are carried out in series. It is preferable to use water as solvent in the first stage and to add the mercaptan, either pure or dissolved in an organic solvent or solvent mixture, to the reaction mixture obtained which contains the gold(I) halogen sulfide complex in dissolved form and optionally also in suspended form. In selected instances, the two method stages can also be carried out parallel to one another, as was suggested in DE-AS 12 98 828; this embodiment assumes that the added mercaptan practically does not react in the manner of the method principle of formula scheme A. Although the sulfide can be added in excess, usually only two moles sulfide per mole AU(III) halogenide or AU(III) halogen complex are used for considerations of economy. The mercaptan is generally added to the gold in equimolar amount, although an excess of mercaptan is not excluded.

Both reaction stages are carried out in a temperature range between $-20°$ and $40°$ C., preferably between $0°$ and $20°$ C. The temperature does not have to be identical in the two stages.

In order to prepare gold(I) mercaptides such as e.g. gold(I) isopropyl mercaptide which are only slightly soluble in organic solvents, the second reaction stage is carried out. This is done preferably either in the absence of an organic solvent or in the presence of an organic solvent mixture which forms a homogeneous liquid phase with the water from the first reaction stage and consists of a solvent immiscible with water and of a solvent miscible with water. Among the solvents immiscible with water, aromatic and aliphatic hydrocarbons, chlorinated hydrocarbons and ether suitable, and among the solvents miscible with water $C_1$- to $C_4$-alcohols, $C_3$- to $C_5$-ketones, N-alkylpyrrolidones and dimethylsulfoxide are suitable. The gold(I) mercaptide which precipitated from the clear reaction solution is separated by means of filtering or centrifuging from the liquid reaction medium, washed and dried, generally below $50°$ C.

Gold(I) mercaptides such as e.g. gold(I) tert.-dodecyl mercaptide which are readily soluble in organic solvents are preferably prepared in the presence of non-water-soluble organic solvents from the above-named series. The reaction thus takes place in the two-phase system and the gold(I) mercaptide dissolved in the organic phase can be obtained by removing the solvent.

The stereospecific oxidation of D- and L-methionine to the corresponding sulfoxide by means of tetrachloro auric acid is known from J. Chem. Soc. Chem. Comm. 1973, p. 878. No suggestions for using methionine as sulfide in the method of the present invention for preparing gold(I) mercaptides can be gathered from this document.

It could not have been foreseen that the alkyl mercapto amino acids in accordance with the present invention form stable gold(I) halogenide complexes which can be reacted with mercaptans of very different structure in a high yield and high space-time yield to form gold(I) mercaptides. A prominent advantage of the alkyl mercapto amino acids lies in their water solubility on the one hand and insolubility in organic solvents on the other hand. As a result thereof, the gold(I) mercaptides can be separated in a simple manner from the liberated alkyl mercapto amino acid as well as its sulfoxide and purified. The previously required necessary expense for purification as well as the necessary amount of solvent were able to be reduced and the purity of the gold(I) mercaptide as well as the yield and the space-time yield were able to be increased. A further advantage is the moderate odor of the alkyl mercapto amino acids, which enables a work environment without odor problems. The method of the present invention can be used independently of the structure and the solubility of the gold(I) mercaptides with good success for their preparation.

EXAMPLES

Example 1 and Reference Example 1

Preparation of gold(I) isopropyl mercaptide

The reduction and complex formation were carried out in water by adding an aqueous solution of tetrachloro auric acid drop by drop at 50° C. to a solution or emulsion of sulfide. The mercaptan was then added drop by drop. The batch amounts and results as well as purification measures as shown in the following table:

|  | Example 1 | Reference example 1 according to DE-AS 12 86 866 |
|---|---|---|
| 1st stage: | | |
| | 59.7 g (0.4 mole) D,L-methionine | 54.0 g (0.6 mole) diethyl sulfide |
| | 68.0 g (0.2 mole) HAuCl$_4$ | 68.0 g (0.2 mole) HAuCl$_4$ |
| | 1000 g water | 1000 g water |
| 2nd stage: | | |
| | 15.2 g (0.2 mole) 2-propanethiol | 16.8 g (0.22 mole) 2-propanethiol |
| | 20.0 g dichloromethane | |
| | 20.0 g ethanol | |
| Purification: | | |
| | wash 1 × with 100 ml ethanol | wash 3 × with 300 ml water per time wash 2 × with 500 ml methanol per time wash 1 × with 300 ml methanol per time |
| | Au content: 72.4% | 72.4% |
| | Yield: 89.0% (relative to reacted gold) | 74.0% |

EXAMPLE 2 AND REFERENCE EXAMPLE 2

Preparation of Gold(I) tert.-dodecyl mercaptide

The method is carried out analogously to that of example 1 and reference example 1. The batches, purification measures and results are shown in the following table:

|  | Example 2 | Reference example 2 according to DE-AS 12 98 828 |
|---|---|---|
| 1st stage: | | |
| | 59.7 g (0.4 mole) D,L-methionine | 37.3 g (0.6 mole) diethyl sulfide |
| | 68.0 g (0.2 mole) HAuCl$_4$ | 60.7 g (0.2 mole) AuCl$_3$ |
| | 1000 g water | 1000 g water |
| 2nd stage: | | |
| | 43.5 g (0.2 mole) tert.-dodecyl mercaptan | 43.5 g (0.22 mole) tert.- dodecyl mercaptan |
| | 100 g dichloromethane | 30 g chloroform |
| Purification: | | |
| | none (only distilling off of the CH$_2$Cl$_2$) | wash 3 × with 300 ml water per time at 50° C. wash 1 × with 150 ml methanol reprecipitation 1 × by dissolving in 50 ml chloroform and precipitating with 1200 ml methanol |
| | Au content: 48.6% | 48.2% |
| | Yield: 98.0% | 97.0% |

Further variations and modifications of the invention will become apparent to those skilled in the art from the foregoing and are intended to be encompassed by the claims appended hereto.

What is claimed is:

1. A method for the preparation of gold(I) mercaptides of the formula Au—S—R, in which R is an organic group and the sulfur atom is bound to an aliphatic, cycloapliphatic or aromatic carbon atom of the organic group, comprising:
    (a) reacting a gold(III) halogenide or gold(III) halogen complex with a sulfide in a molar ratio of 1:2 to 1:3 in the presence of an amount of water at least equivalent to the Au(III) compound at −20° to 40° C. to form a gold(I) halogenide- sulfide complex and a sulfoxide of said sulfide,
    (b) reacting said gold(I) halogenide sulfide complex at −20° to 40° C., optionally in the presence of an organic solvent or solvent mixture, with a mercaptan of the formula RSH, in which R has the same meaning as in said gold(I) mercaptides, to form a gold (I) mercaptide, and
    (c) isolating said gold(I) mercaptide; wherein said sulfide is water soluble and is a (C$_1$- to C$_8$-) alkyl mercapto-(C$_3$- to C$_6$-) amino acid in which the alkyl mercapto- and the amino group are bound to different C atoms, or a water-soluble salt thereof.

2. The method according to claim 1, wherein the alkyl group of said alkyl mercapto is (C$_{1-4}$).

3. The method according to claim 2, wherein the alkyl group of said alkyl mercapto is methyl.

4. The method according to claim 1, wherein the amino acid is (C$_{3-4}$).

5. The method according to claim 1, wherein said sulfide is methyl mercapto-(C$_3$-or C$_4$-) amino acid.

6. The method according to claim 1, wherein said sulfide is D,L methionine or S-alkylated cysteine.

7. The method according to claim 1, wherein said mercapto amino acid is in the D,L form.

8. The method according to claim 1, wherein said salt is a salt of said mercapto amino acid with an acid selected from the group consisting of hydrohalic acid, sulfuric acid, phosphoric acid, and perchloric acid.

9. The method according to claim 1, wherein said salt is a alkali or ammonium salt.

10. The method according to claim 1, wherein said gold (III) halogenide is $AuCl_3$, $AuBr_3$ or $AuI_3$.

11. The method according to claim 1, wherein said gold (III) halogen complex is $HAuCl_4$, $HAuBr_4$, or $HAuI_4$.

12. The method according to claim 1, wherein said gold (III) halogen complex is a complex of a neutral ligand and $AuCl_3$, $AuBr_3$ or $AuI_3$.

13. The method according to claim 12, wherein said neutral ligand is tertiary amine or tertiary phosphine.

14. The method according to claim 1, wherein said molar ratio is 1:2.

15. The method according to claim 1, wherein the ratio of said mercaptan to said gold (I) halogenide sulfide complex is from 1:1 to 1:2.

16. The method according to claim 15, wherein the ratio of said mercaptan to said gold (I) halogenide sulfide complex is 1:1.

17. The method according to claim 1, wherein either or both of said temperature ranges is 0° to 20° C.

18. The method according to claim 1, wherein said solvent mixture comprises a solvent immiscible with water and a solvent miscible with water.

19. The method according to claim 18, wherein said solvent immiscible with water is selected from the group consisting of aromatic and aliphatic hydrocarbons, chlorinated hydrocarbons, and ether.

20. The method according to claim 18, wherein said solvent miscible with water is selected from the group consisting of $C_{1-4}$ alcohols, $C_{3-5}$ ketones, N-alkylpyrrolidones, and dimethylsulfoxide.

21. The method according to claim 1, wherein step (c) does not utilize a washing step.

22. The method according to claim 1, wherein step (c) utilizes only one washing step.

* * * * *